US008874193B2

United States Patent
Popescu (10) Patent No.: US 8,874,193 B2
(45) Date of Patent: Oct. 28, 2014

(54) IMAGE RECORDING DEVICE FOR THE SIMULTANEOUS RECORDING OF MAGNETIC RESONANCE IMAGE DATA AND NUCLEAR MEDICAL IMAGE DATA

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 232 days.

(21) Appl. No.: 13/434,152

(22) Filed: Mar. 29, 2012

(65) Prior Publication Data
US 2012/0253174 A1 Oct. 4, 2012

(30) Foreign Application Priority Data

Mar. 30, 2011 (DE) .......................... 10 2011 006 435

(51) Int. Cl.
*A61B 5/00* (2006.01)
*G01R 33/48* (2006.01)
*A61B 6/00* (2006.01)
*A61B 6/03* (2006.01)
*A61B 5/055* (2006.01)

(52) U.S. Cl.
CPC ............ *G01R 33/481* (2013.01); *A61B 6/4417* (2013.01); *A61B 6/508* (2013.01); *A61B 6/037* (2013.01); *A61B 6/42* (2013.01); *A61B 5/0035* (2013.01); *A61B 6/502* (2013.01); *A61B 5/055* (2013.01); *A61B 5/0071* (2013.01); *A61B 6/501* (2013.01); *A61B 6/481* (2013.01)
USPC ........... 600/436; 600/407; 600/410; 600/411; 600/425; 600/427

(58) Field of Classification Search
USPC ................. 600/407, 410, 411, 425, 427, 436
See application file for complete search history.

(56) References Cited

U.S. PATENT DOCUMENTS

| 7,719,277 | B2 | 5/2010 | Eberler et al. |
| 8,041,414 | B2 * | 10/2011 | Peter et al. ..................... 600/427 |
| 8,287,471 | B2 * | 10/2012 | Liu et al. ........................... 601/3 |
| 2008/0208032 | A1 | 8/2008 | Schuster et al. |
| 2009/0221903 | A1 | 9/2009 | Corbeil et al. |
| 2010/0092809 | A1 | 4/2010 | Drzal et al. |

(Continued)

FOREIGN PATENT DOCUMENTS

| DE | 102006037047 A1 | 2/2008 |
| DE | 102007009180 A1 | 8/2008 |

(Continued)

OTHER PUBLICATIONS

Simon R. Cherry: Multimodality Imaging: Beyond PET/CT and SPECT/CT, Semin Nucl. Med. Sep. 2009; 39(5):348-353. doi: 10.1053/j.semnuclmed.2009.03.001.http://www.ncbi.nlm.nih.gov/pmc/articles/PMC2735449/; Others; 2009.

(Continued)

*Primary Examiner* — Peter Luong
(74) *Attorney, Agent, or Firm* — Harness, Dickey & Pierce (57) ABSTRACT

An image recording device is disclosed for the simultaneous recording of magnetic resonance image data and nuclear medical image data, in particular PET image data. In at least one embodiment, the image recording device includes a nuclear medical detector arrangement integrated into a magnetic resonance device, wherein a fluorescence detector arrangement including an optical system and designed for fluorescence imaging is also integrated into the magnetic resonance device.

21 Claims, 5 Drawing Sheets

(56) References Cited

U.S. PATENT DOCUMENTS

| | | |
|---|---|---|
| 2010/0292563 A1 | 11/2010 | Stuker et al. |
| 2011/0270077 A1* | 11/2011 | Kang et al. .................... 600/411 |
| 2012/0150017 A1* | 6/2012 | Yamaya et al. ............... 600/411 |

FOREIGN PATENT DOCUMENTS

| | | |
|---|---|---|
| DE | 102008012312 A1 | 1/2010 |
| EP | 2062032 B1 | 6/2010 |
| EP | 2251676 A1 | 11/2010 |
| WO | WO 2006111485 A2 | 10/2006 |
| WO | WO 2008028904 A1 | 3/2008 |
| WO | WO 2010079251 A1 | 7/2010 |

OTHER PUBLICATIONS http://www.research.philips.com/newscenter/archive/2009/backgrounders/091029-hyperimage.html; Others; 2009.

Niedre M. et al.: Elucidating Structure and Function in Vivo With Hybrid Fluorescence and Magnetic Resonance Imaging, vol. 96, IEEE, Mar. 2008; Others; 2008.

Pichler Bernd et al.: PET/MRI: "The Next Generation of Multimodality Imaging?", vol. 38, 2008(3), pp. 199-208. ISBN 1558-4623; Others; 2008.

Philips—http://www.hybrid-pet-mr.eu/index.php?id=workpackages; Others; Sep. 1, 2008.

\* cited by examiner

IMAGE RECORDING DEVICE FOR THE SIMULTANEOUS RECORDING OF MAGNETIC RESONANCE IMAGE DATA AND NUCLEAR MEDICAL IMAGE DATA

PRIORITY STATEMENT

The present application hereby claims priority under 35 U.S.C. §119 to German patent application number DE 10 2011 006 435.4 filed Mar. 30, 2011, the entire contents of which are hereby incorporated herein by reference.

FIELD

At least one embodiment of the invention generally relates to an image recording device for the simultaneous recording of magnetic resonance image data and nuclear medical image data, in particular PET image data, comprising a nuclear medical detector arrangement integrated into a magnetic resonance device.

BACKGROUND

The combination of structural imaging with functional and molecular imaging allows functional or molecular information to be assigned to specific anatomical structures, such as tissues or organs, so that, ultimately, structure-function relationships can be recorded. Clinical examples already used include the combination of structural and functional magnetic resonance imaging, wherein areas of the brain for example which have been activated by specific excitation are superimposed with high-resolution anatomical images. Another example is the combination of positron emission tomography (PET) with computer tomography (CT), which makes it possible to identify areas of altered metabolic activity within the overall anatomical system. Image recording devices which combine magnetic resonance (MR) and PET are currently being tested in a clinical environment.

PET and SPECT (single photon emission computed tomography) are examples of nuclear medical imaging techniques which primarily map functional processes in an object under examination. With PET, images of living organisms are produced, which make it possible to visualize the distribution of a previously administered, weakly radioactively labeled substance in the organism, said substance having been enriched in the organism in such a way that biochemical and physiological processes can be mapped. Radionuclides which emit positrons during decay are used as the substance (tracer) in this case. After a short distance, for example 2 to 3 mm, the positrons interact with an electron, resulting in "annihilation". Both particles (positron and electron) are destroyed, and two high-energy photons (gamma radiation) are formed with an energy of 511 keV each. These photons move away from one another at an angle of approx. 180°. Both photons are measured, for example using a detector ring, whereby two different points of the detector ring are contacted at the same time. It is possible to detect positron emission and to estimate the point of annihilation on the basis of the coincidence of the two measurements.

It has also been proposed to form systems which allow simultaneous nuclear medical imaging and fluorescence imaging (often also referred to as optical imaging). With fluorescence imaging, a fluorescent or bioluminescent substance is excited to fluorescence within the body using excitation light, whereupon light of a certain wavelength is emitted. This light can be detected, and therefore an image is ultimately formed which shows where the excited substance is located.

The combining of nuclear medical imaging with fluorescence imaging is motivated by the fact that different molecular targets are to be measured at the same time and that imaging techniques are sought which can be used as a kind of "translation platform" between the widely used optical imaging techniques, which use bioluminescent or fluorescent reporter substances or injected fluorescent substances, and nuclear medical examinations using a radiotracer. Tomographic imaging instruments for small animals, which combine optical imaging and PET, or optical imaging and SPECT with one another, have already been proposed in this regard. One possible clinical use of such hybrid technologies would be, for example, the use of the sensitive whole-body potential of PET or SPECT to carry out an "optical biopsy" using an endoscope or a catheter having an optical imaging device, so that, ultimately, it is possible to achieve local "mapping" of fluorescence signals with high resolution and high sensitivity at points which were already noticeable in the PET or SPECT scan.

Since magnetic resonance imaging offers good structural resolution, it has also been proposed to combine optical imaging, that is to say fluorescence imaging using bioluminescent or fluorescent substances, with magnetic resonance imaging. In this way, high-resolution three-dimensional structural imaging can be combined with optical imaging, wherein fields of application range from the imaging of small animals to the provision of recorded images of the human breast or the human brain. Since a spatially resolved three-dimensional reconstruction of the diffuse fluorescence images is ultimately impossible on this basis alone, the spatially recorded magnetic resonance images can be used to locate the boundaries of tissues having different optical properties and thus to increase the accuracy of three-dimensional fluorescence reconstruction.

Contrast agents which are suitable for imaging with a number of modalities are also being examined in conjunction with these hybrid modalities. A number of large biomolecules, such as peptides or proteins, and of particles, such as microbubbles, liposomes and nanoparticles, form suitable platforms for producing contrast agents which can provide a contrast for more than one imaging modality. The motivation for the development of these contrast agents lies in the fact that they allow examination of the same target using a single contrast agent on different imaging platforms and on different scales. For example, such a contrast agent suitable for a number of modalities can be administered to then carry out fluorescence imaging and to later carry out magnetic resonance imaging, PET or SPECT by way of the same contrast agent. Another possibility for the use of these contrast agents can be found in imaging devices which combine different imaging modalities. For example, in a combined PET/MR system, the high sensitivity of PET can be used to locate areas of high uptake of a PET/MR contrast agent in the body, whereupon high-resolution magnetic resonance imaging of said contrast agent is possible, wherein the magnetic resonance images must be recorded only in the areas where the PET signal was observed.

A large number of hybrid contrast agents which are suitable for optical imaging, that is to say fluorescence imaging, and for magnetic resonance have already been proposed. Examples include fluorescent quantum dots with a paramagnetic coating, quantum dots with high native relaxivity, lipoproteins containing iron oxide nanoparticles and quantum dots, liposomes containing gadolinium and fluorescence agents, as well as antibodies which are provided with both magnetic nanoparticles and fluorescence agents. In some cases these particles and proteins are additionally being designed to include radionuclides suitable for PET or SPECT imaging.

PET detector arrangements known in the prior art include, for example, an array of scintillator blocks, which convert the energy of incident gamma photons into low-energy photons of visible light. This visible light is then captured by a photodetector, which may be a CCD (charge coupled device) detector, an APD (avalanche photo diode) detector, or a CMOS (complementary metal oxide semiconductor) sensor, for example.

As already mentioned, image recording devices which are designed for simultaneous magnetic resonance and PET imaging are also already known in the prior art. A large number of designs are known. It has been proposed, for example, to divide the gradient coil of a magnetic resonance device into two halves, wherein the PET detector ring is provided in the gap between the two portions of the gradient coil arrangement. A radio frequency shield, which completely surrounds the radio frequency coil and blocks the radio frequency signals of the coil but does not substantially weaken the γ-photons of PET, separates the radio frequency coil (body coil) from the gradient coil arrangement and the PET detector ring.

A shell-like structure of a combined MR/PET device was proposed in another known device. In this case, the PET detector arrangement is provided as a tubular insert between the gradient coil arrangement and the radio frequency body coil. The radio frequency shield separates the body coil from the PET insert. The gradient coil arrangement defines the outer diameter of the PET insert. In the known MR/PET device, the PET detector arrangement consists of detector blocks with an LSO scintillator crystal and a highly sensitive APD photodetector array with associated electronics. The radio frequency shield and the conductors of the body coil consist of thin copper strips, which are almost completely transparent to the 511 keV photons of PET.

Another combined image recording device, in which a PET detector arrangement is integrated into a magnetic resonance device, is known from U.S. Pat. No. 7,719,277. This concerns a compact solution, in which the PET detector blocks of the PET detector arrangement have gaps in which the longitudinal conductors (often also called "rods") of the coaxially disposed radio frequency coil arrangement are guided. The detector unit, which consequently contains the body coil and the PET detector arrangement, is formed as a tubular insert which is separated from the gradient coil arrangement by the radio frequency shield. The radio frequency shield is folded over laterally to shield the PET electronics from the radio frequency coils of the body coil.

An image recording device having two imaging modalities is also known from WO 2008/028904 A1. It is proposed to provide a magnetic resonance device having at least one optical imaging detector, wherein the magnetic resonance data and the optical image data of an object are to be recorded at the same time. The magnetic resonance device comprises a magnet for generating a static magnetic field in an imaging volume of the magnetic resonance device, gradient coils for generating magnetic gradient fields, and a radio frequency coil which is arranged within the imaging volume so as to surround an object. At least one subsystem of the at least one optical imaging detector is to be arranged within the imaging volume, so that optical photons emitted from the object to be imaged can be received through an opening in the radio frequency coil. The microlens array used for this purpose is to be integrated into the radio frequency coil.

Starting from this prior art, the object of the present invention is to create an image recording device which allows progressive advantageous combination of different imaging modalities.

SUMMARY

At least one embodiment of the invention is directed to a fluorescence detector arrangement including an optical system and designed for fluorescence imaging is also integrated into the magnetic resonance device in an image recording device of the type mentioned at the outset.

At least one embodiment of the invention therefore proposes, for the first time, to allow magnetic resonance imaging, a nuclear medical type of imaging, particularly PET, and fluorescence imaging (including imaging by bioluminescence) using a single image recording device. More specifically, a fluorescence detector arrangement is also to be integrated into a magnetic resonance device in addition to a nuclear medical detector arrangement. In this way, a wide range of complementary imaging methods are combined with one another. While magnetic resonance imaging delivers high-resolution structural information and functional information, further functional and molecular information can be provided by nuclear medical imaging advantageously supplemented by molecular information obtained by fluorescence imaging. It is not necessary to move the patient between the recordings of images by way of the various imaging techniques, and the resultant images can be linked directly with one another. A versatile image recording device with an extremely broad field of application is thus created.

In a particularly expedient embodiment of the image recording device according to the first embodiment, the image recording device is constructed according to the shell principle, wherein, starting from a cylindrical patient receptacle, at least part of the fluorescence detector arrangement permeable to the γ-photons to be detected for nuclear medical imaging is provided first, while the nuclear medical detector arrangement follows in a shell arranged further outwardly. The shell principle already known ultimately from the prior art is thus extended so as to also allow the recording of fluorescence images. The components of the fluorescence detector arrangement arranged in the path of the γ-photons to be detected by the nuclear medical detector arrangement are produced in particular from a low density material, wherein the optical system of the fluorescence detector arrangement preferably consists of plastic, at least in part. Sufficient transparency is thus provided for the γ-photons (gamma radiation) to be detected within the scope of nuclear medical imaging.

BRIEF DESCRIPTION OF THE DRAWINGS

Further advantages and details of the present invention will become apparent from the example embodiments described hereinafter and on the basis of the drawings, in which.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the invention therefore proposes, for the first time, to allow magnetic resonance imaging, a nuclear medical type of imaging, particularly PET, and fluorescence imaging (including imaging by bioluminescence) using a single image recording device. More specifically, a fluorescence detector arrangement is also to be integrated into a magnetic resonance device in addition to a nuclear medical detector arrangement. In this way, a wide range of complementary imaging methods are combined with one another. While magnetic resonance imaging delivers high-resolution structural information and functional information, further functional and molecular information can be provided by nuclear medical imaging advantageously supplemented by molecular information obtained by fluorescence imaging. It is not necessary to move the patient between the recordings of images by way of the various imaging techniques, and the resultant images can be linked directly with one another. A versatile image recording device with an extremely broad field of application is thus created.

A suitable optical system for fluorescence imaging usually includes lenses, in particular microlenses, which ultimately define pixels, and optical filters, in particular chromatic filters, which can filter out the light to be captured of the specific fluorescence or luminescence wavelength. Moreover, depending on the specific arrangement, the optical system of the fluorescence detector arrangement may comprise optical waveguide elements, for example to feed the light collected by a microlens to a specific photodetector. By contrast, the optical system of the nuclear medical detector arrangement usually comprises an array of scintillator blocks which convert the γ-photons originating from the nuclear decay processes or annihilation processes into visible light, which is then captured by photodetectors. It should be noted at this point that magnetic resonance compatible photodetectors are, of course, used within the scope of the present invention, as are known in principle from the prior art for combined MR/PET devices.

There are basically two proposed alternatives for the specific embodiment of integration, wherein a simultaneous recording of images using all three image recording modalities is enabled in the first instance, and at least partly sequential operation is provided in the second case, however.

In a first, advantageous alternative embodiment of the present invention, the nuclear medical detector arrangement and the fluorescence detector arrangement can thus be arranged, together with the magnetic resonance device, out of a target area, in particular the homogeneity volume of the magnetic resonance device, for simultaneous data acquisition. Simultaneous magnetic resonance, PET or SPECT, and fluorescence image recording is thus possible. A contrast agent suitable for a number of modalities is particularly preferably used in this case, and therefore the contrast agent is advantageously visible in all images recorded simultaneously, or the visibility of the contrast agent is defined in an image recorded using one modality, in the target area of which a different image is to be recorded.

In a particularly expedient embodiment of the image recording device according to the first embodiment, the image recording device is constructed according to the shell principle, wherein, starting from a cylindrical patient receptacle, at least part of the fluorescence detector arrangement permeable to the γ-photons to be detected for nuclear medical imaging is provided first, while the nuclear medical detector arrangement follows in a shell arranged further outwardly. The shell principle already known ultimately from the prior art is thus extended so as to also allow the recording of fluorescence images. The components of the fluorescence detector arrangement arranged in the path of the γ-photons to be detected by the nuclear medical detector arrangement are produced in particular from a low density material, wherein the optical system of the fluorescence detector arrangement preferably consists of plastic, at least in part. Sufficient transparency is thus provided for the γ-photons (gamma radiation) to be detected within the scope of nuclear medical imaging.

In the longitudinal direction of the patient receptacle, the patient receptacle can preferably be adjoined first by a body coil, in particular with a radio frequency shield, covering the field of homogeneity, the nuclear medical detector arrangement following next to the body coil radially outwardly, wherein the fluorescence detector arrangement comprises the optical system which is integrated into the body coil, in particular arranged between longitudinal conductors of the body coil, and which has a connecting optical waveguide system which is designed to guide the fluorescent light received by the optical system to a photodetector arrangement arranged in the longitudinal regions not covering the field of homogeneity, in particular in the radial region of the nuclear medical detector arrangement, or outside the magnetic resonance device. This embodiment allows a particularly compact design which allows for a larger patient receptacle, which is often desired.

At this juncture, the basic idea presented by WO 2008/028904 A1 and DE 10 2006 037 047 A1, the entire contents of each of which are hereby incorporated herein by reference, to integrate at least parts of a detector arrangement into the body coil of the magnetic resonance device, wherein the gaps between longitudinal conductors of the body coil, formed in particular as a birdcage, can be utilized for example, is developed further, in principle, by at least one embodiment of the present invention. It should be noted that the field of homogeneity (often also called the field of view of the magnetic resonance device) does not cover the entire length of the patient receptacle, and therefore the body coil and the PET detector arrangement, to which the gradient coil arrangement may be adjoined radially outwardly, do not have to fill the entire longitudinal length of the patient receptacle in order to cover the field of homogeneity, but instead a gap remains in the edge regions of the patient receptacle which is advantageously used within the scope of at least one embodiment of the present invention for arrangement of the photodetectors of the fluorescence detector arrangement in order to further improve, in this specific example embodiment, the compact design and excellent utilization of space.

In order to ultimately allow simultaneous use of three modalities, the optical system of the fluorescence detector arrangement is consequently connected to an optical waveguide system which may comprise optical cables, in particular with a plurality of optical fibers, and tappers so as to feed the visible incident light, which is produced by the fluorescence of the object under examination, to the corresponding photodetectors of the photodetector arrangement arranged longitudinally outside the field of homogeneity. More specifically, the optical system can be designed in this case so that it comprises a plurality of microlenses arranged in at least one microlens array, wherein in particular each microlens is connected to an optical fiber of the optical waveguide system. Each of the microlenses thus ultimately defines a "pixel", since the light captured by each microlens can be detected in a spatially resolved manner. Further embodiments of such an optical waveguide system are known in principle from WO 2008/028904 A1 and can also be used in the present case.

In a second embodiment, alternative to the first embodiment, at least some of the modalities are used sequentially. More specifically, at least one displacement device for selectively bringing at least part of either the nuclear medical detector arrangement or the fluorescence detector arrangement into an imaging position, in particular covering a field of homogeneity of the magnetic resonance device, may be provided. At least part of the nuclear medical detector arrangement and part of the fluorescence detector arrangement are consequently designed so as to be displaceable, and therefore the fluorescence detector arrangement or the nuclear medical detector arrangement are able to selectively record image data from the field of homogeneity (field of view).

In this embodiment, it is generally advantageous if the fluorescence detector arrangement and the nuclear medical detector arrangement have a common photodetector arrangement, which means that the photodetector arrangement, which is stationary in particular, is used for both imaging modalities. As part of the detector arrangements, the optical systems thereof can be displaced particularly advantageously, so that, in the case of a photodetector arrangement covering the field of homogeneity of the magnetic resonance device, the light to be detected is supplied either by the optical system of the fluorescence detector arrangement or by the optical system of the nuclear medical detector arrangement.

This is particularly advantageous with a design of the magnetic resonance device according to the shell principle, wherein the photodetector arrangement can preferably be arranged radially inwardly beside a gradient coil arrangement of the magnetic resonance device, whereas the optical systems of the detector arrangements share a shell in which they can be displaced longitudinally in the longitudinal direction of the patient receptacle by the displacement device. As already discussed, this is based on the fact that the field of homogeneity of the magnetic resonance device does not normally take up the entire length of the patient receptacle, and therefore the unused edge region can be used to "park" the currently unused part of a detector arrangement, in particular the optical system of a detector arrangement. Where appropriate, the length of the patient receptacle can be adapted to provide sufficient space in the longitudinal direction.

Particularly with regard to the shell-like structure just described, in which the optical systems of the detector arrangements share one shell, there are basically two alternatives of this second embodiment of the present invention which can be used. On the one hand, a body coil, in particular a body coil comprising a radio frequency shield, of the magnetic resonance device is displaceable together with the nuclear medical detector arrangement. There are two modes for this, wherein, in the first mode, simultaneous magnetic resonance/PET imaging is possible, and in the second mode only optical imaging is possible. The displacement device, for example a shuttle actuator, is used to switch between the modes.

In this case, as already mentioned, the optical systems of the detector arrangements are advantageously displaced in front of a commonly used photodetector arrangement, wherein, in the first mode, the displacement device moves the optical system of the fluorescence detector arrangement out of the field of homogeneity, and the optical system, in particular comprising an array formed of scintillator blocks, of the nuclear medical detector arrangement is placed in front of the photodetector arrangement, whereas the body coil, with its shield, is brought into the field of homogeneity. In this case, the photodetectors of the photodetector arrangement consequently detect the incident gamma radiation photons, which are converted into visible light by the scintillator blocks. In the second mode, the displacement device replaces the scintillators and the radio frequency system with the optical system used in fluorescence imaging, which may comprise optical lenses, in particular microlenses, chromatic filters and light sources, for example. Consequently, fluorescence imaging is then possible.

Nevertheless, it should be noted at this juncture that a common photodetector arrangement for the fluorescence detector arrangement and for the nuclear medical detector arrangement is not necessary. The entire detector arrangements may also be displaceable within and adjacent to a gradient coil arrangement. Special photodetectors can also be used for both imaging methods.

On the other hand, in an alternative, example embodiment, an optical system, comprising an array of scintillator blocks, of the nuclear medical detector arrangement and the optical system, comprising microlenses in particular, of the fluorescence detector arrangement may be selectively displaceable, as a part of the detector arrangements, in regions of the stationary body coil not occupied by elements of a body coil, in particular between longitudinal conductors of the body coil, wherein a photodetector arrangement used jointly for nuclear medical imaging and fluorescence imaging adjoins the body coil, in particular a radio frequency shield of the body coil, radially outwardly. This alternative of the invention functions similarly to the previously described alternative, only two modes now being provided, simultaneous imaging being possible in both modes, namely magnetic resonance/PET imaging in one mode, and fluorescence/MR imaging in the other mode. Spaces in the body coil, which is stationary in principle, are used for the introduction of suitable optical systems. In this case, too, the optical system of the fluorescence detector arrangement is moved out of the field of homogeneity and out of the region of the body coil by the displacement device in the first mode, and the scintillator array is arranged in front of the photodetector arrangement used jointly, in particular between the longitudinal conductors of the body coil.

Here, too, gamma radiation photons of nuclear medical imaging are consequently converted into visible light by the scintillator blocks and can be detected accordingly. In the second mode, the scintillator array is replaced with the optical system of fluorescence imaging, which may comprise optical lenses, in particular microlenses, chromatic filters and light sources, for example. In this regard it is advantageous if the radio frequency shield consists of an optically transparent, electrically conductive layer. Such layers may have high absorption/reflection for incident electromagnetic radiation in the range of the larmor frequency of the magnetic resonance device, that is to say in the range relevant for magnetic resonance imaging. Such layers are known in principle in the prior art and reference is made, for example, to US 2010/0092809 A1, the entire contents of which are hereby incorporated herein by reference, which describes electrically conductive, optically transparent layers formed of graphite nanoparticles.

When using a displacement device, the displacement device may generally comprise at least one guide in which a support for the components to be displaced is guided. This can be achieved advantageously, in particular if a structure according to the shell principle is provided, so that a suitable guide, which spans the entire or required longitudinal length of the patient receptacle, can be provided within a shell for example, wherein the arrangements to be displaced, in particular the optical systems, are arranged in succession in the longitudinal direction in a support guided in the guide. The required arrangement can thus always be displaced or moved into the imaging position, covering the field of homogeneity.

The support "shuttles" so to speak between two imaging positions. It should be noted at this juncture that such a purely longitudinal displacement in the longitudinal direction of the patient receptacle is also conceivable if a stationary body coil, in particular a birdcage coil, is used, since the outwardly terminating conductor rings can be designed accordingly to provide a suitable geometry.

Furthermore, the displacement device may comprise an electric and/or hydraulic and/or pneumatic drive device, wherein, in the case of an electric drive device, the electrical components are arranged outside a patient receptacle of the magnetic resonance device. A wide range of various possibilities are thus conceivable with regard to the specific formation of the displacement device, wherein hydraulic and/or pneumatic drive devices are preferred, since interaction with the magnetic fields of the magnetic resonance can be largely avoided.

Generally, the optical system may comprise at least one light diffuser for optical excitation light, said light diffuser being connected via an optical waveguide to a light source, in particular at least one laser. The fluorescent substance is excited in the object to be examined via an optical excitation light of this type so as to emit fluorescent light. Lasers are normally coupled to light diffusers for this purpose, said light diffusers enabling uniform illumination of the object to be examined, and therefore enabling uniform illumination of the field of homogeneity in particular in the present case, for which purpose they may form part of the optical system of the fluorescence detector arrangement. It should be noted that it is of course equally possible to arrange the light diffusers or light sources for the optical excitation light at another location, provided sufficient illumination with excitation light of the object under examination is possible.

The optical arrangement may also particularly advantageously comprise at least one optical element which can be focused on a specific target area and which is actuatable via a mechanical actuator, the actuators being controllable by a control device of the image recording device, in particular according to an assessment of a magnetic resonance image. The optical system of the fluorescence detector arrangement may therefore comprise mechanical actuators, for example so as to adapt the focal distance or position of lenses, in particular microlenses, for optimum focusing on the target area. Adaptive focusing, which uses information which can be derived from a previous magnetic resonance image illustrating the anatomy to be examined in greater detail, can be achieved. A fully automatic assessment is also possible in this instance via a control device which automatically assesses the magnetic resonance image, in particular with regard to a target under examination, so as to use the information in addition to automatically allow a correct setting of the optical system of the fluorescence detector arrangement.

Figure 1:
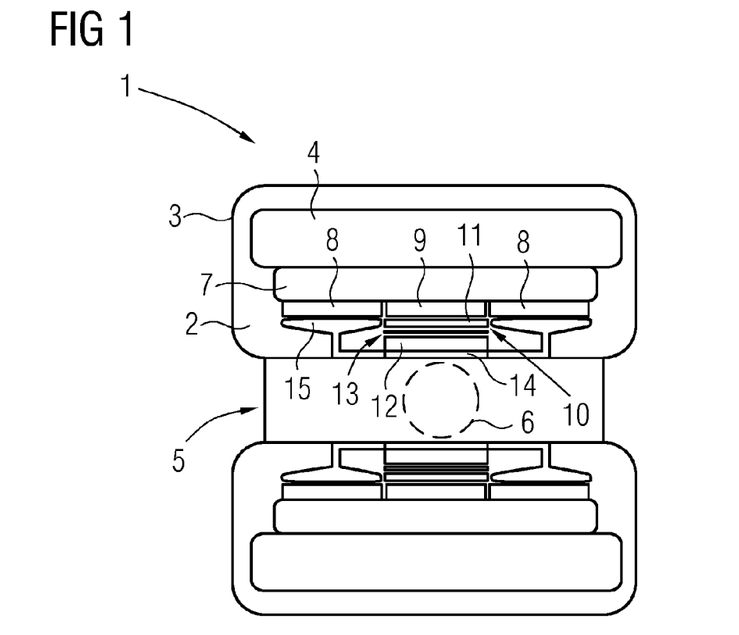
FIG. 1 shows a schematic view of a first example embodiment of an image recording device according to the invention.

FIG. 1 shows a schematic view of a first example embodiment of an image recording device 1 according to the invention. It comprises a magnetic resonance device 2, in which a PET detector arrangement and a fluorescence detector arrangement are integrated. The cylindrical patient receptacle 5 is defined by a housing 3, which also contains the primary magnet 4. The field of homogeneity 6 of the magnetic field generated by the magnet 4 (the field of view—FOV) is also located in said patient receptacle and is merely indicated in this instance. The overall design is selected according to the shell principle, which means that different components of the image recording device are arranged in succession in radial regions. A gradient coil arrangement 7 is the first to adjoin the magnet 4 inwardly, three annular circumferential photodetector arrangements 8, 9, which are arranged in a shell, then adjoining said gradient coil arrangement. The central photodetector arrangement 9 is part of the PET detector arrangement and clearly covers the field of homogeneity 6 completely in the longitudinal direction. The detector arrangements 8 in the outer regions of the patient receptacle 6 in the longitudinal direction are part of the fluorescence detector arrangement. All photodetectors used are compatible with magnetic resonance, as is known.

An array 11 of scintillator blocks adjoins inwardly, upstream of the photodetector arrangement 9, as an optical system 10 of the PET detector arrangement. The body coil 12 formed in this case as a birdcage coil and having a radio frequency shield 13 is located further radially inwardly and also covers the field of homogeneity 6.

Parts of an optical system 14 of the fluorescence detector arrangement are clearly integrated into the body coil 12, more specifically arrays of microlenses, as will be explained in greater detail with the aid of FIGS. 2 and 3, wherein an optical fiber of an optical waveguide system 15 is connected to each microlens, said optical waveguide system leading the fluorescent light captured by way of the microlenses outwardly to the detector arrangements 8. The optical system 14 also comprises chromatic filters for filtering out the frequency of the fluorescent light.

The parts of the optical system 14 which are integrated into the body coil 12, that is to say in particular optical waveguides and optical microlenses, consist of plastic in the present case, as a low density material, and are thus virtually permeable to gamma radiation.

It is clearly possible with the image recording device 1 to simultaneously record magnetic resonance image data, PET image data and fluorescence image data, wherein a multimodal contrast agent can be used particularly advantageously, that is to say a contrast agent which is visible for all three imaging modalities.

Figure 2:
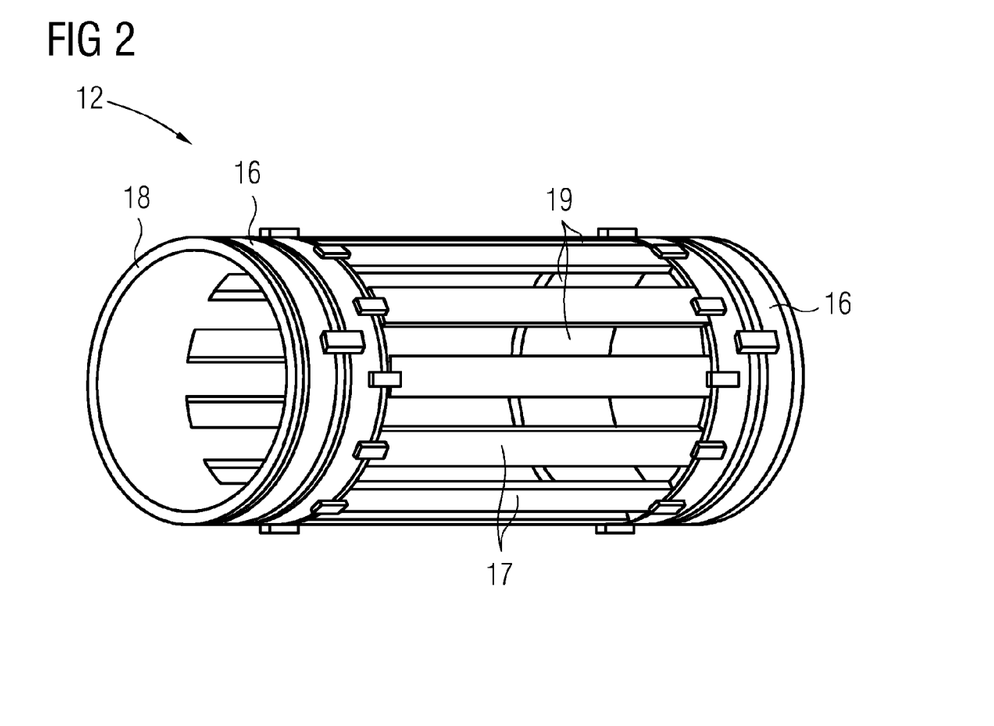
FIG. 2 shows a schematic view of a first example embodiment of a body coil.

FIG. 2 shows more accurately how parts of the optical system 14 are integrated into the body coil 12.

As already mentioned, the radio frequency body coil 12 is constructed in the manner of a birdcage coil and comprises circular end rings 16, which are connected by a series of longitudinal conductors 17. The longitudinal conductors 17 are spaced uniformly from one another. These electrical conductors are made of a thin metal foil, for example a copper foil. They are carried by a substantially cylindrical support structure 18, which may be produced from a non-conductive material, such as epoxy resin. The support structure 18 clearly comprises gaps 19 between the longitudinal conductors 17, said gaps being used in accordance with the invention to fasten the corresponding parts of the optical system 14. Visible light can reach the optical system through the gaps 19.

Figure 3:
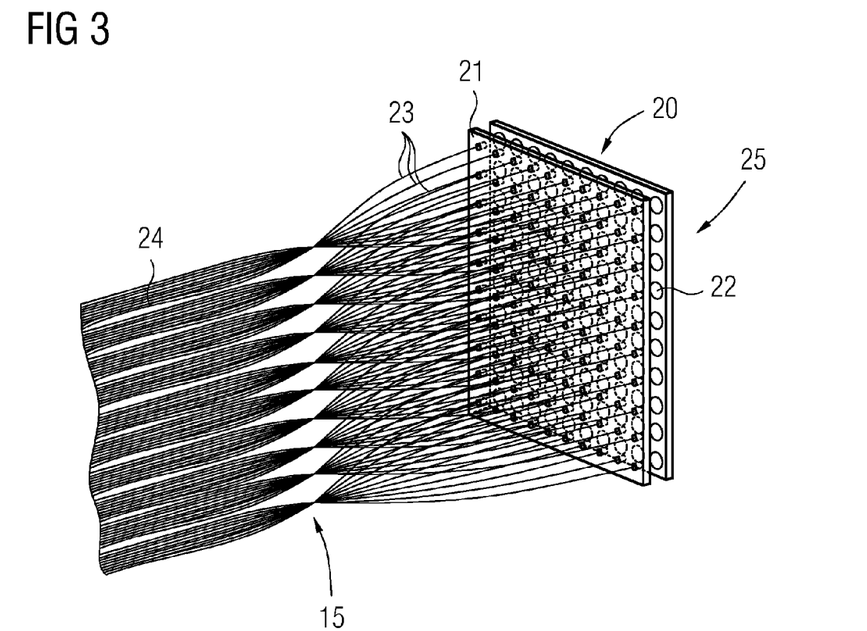
FIG. 3 shows a drawing for the use of arrays of optical microlenses.

More specifically, microlens arrays 20, similar to that shown by way of example in FIG. 3, are arranged in the gaps 19 in the present case. The microlens array 20, which is shown in square form in this case, comprises a plate 21 having a large number of through-holes and a large number of microlenses 22 fixed thereon. A network of optical fibers 23 is provided on the other side of the plate 21, wherein, in each case, an end point of an optical fiber 23 is assigned to the focal point of a microlens 22. The optical fibers 23 are then combined into fiber bundles 24 ("tappers"), which lead the received light to the photodetector arrangement 8 for detection. This means that the optical fibers 23 and the fiber bundles 24 are part of the optical waveguide system 15. Moreover, in an advantageous embodiment the optical waveguide system 15 can also be used to guide excitation light from a light source, such as a laser or a laser diode, onto the object under examination in the magnetic resonance device 2 to excite the fluorescent or bioluminescent substance. In this case, the microlens arrays 20 therefore also serve as light diffusers 25 for excitation light.

Figure 4:
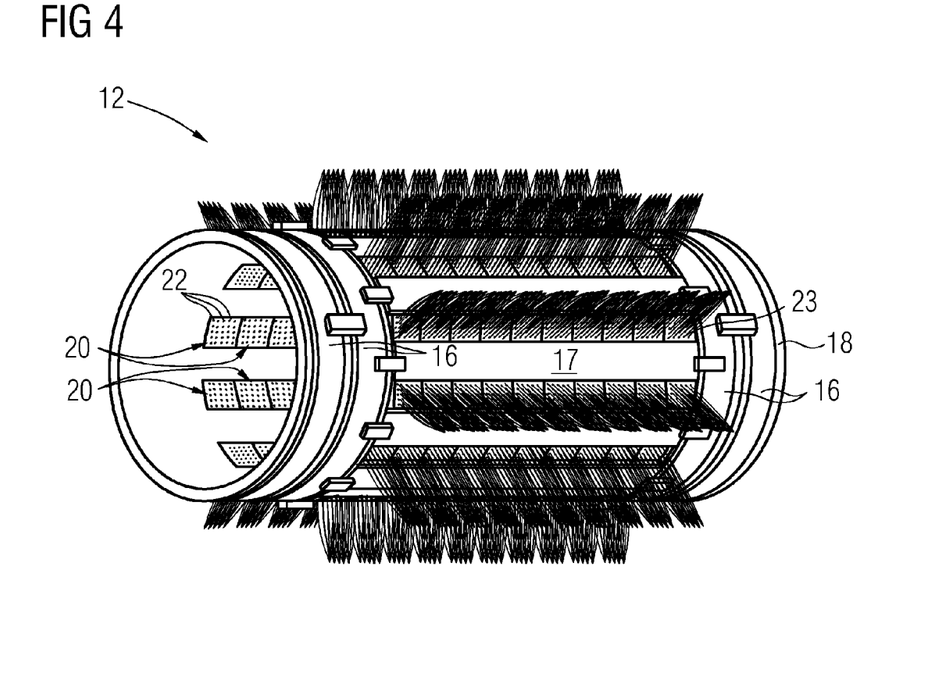
FIG. 4 shows the microlens array of FIG. 3 integrated into the body coil.

FIG. 4 indicates schematically how the microlens arrays 20 can be arranged in the gaps 19 of the body coil 12.

The microlens arrays 20 may comprise, for example, an array of 6×6 microlenses 22, which have a diameter of 1 mm. A plurality of microlens arrays 20 fills a gap 19 in the support structure 18.

It should be noted at this juncture that the basic structure of the optical system 14 with microlens arrays 20 and chromatic filters (not shown in greater detail) is always the same, which means that, even in the case of the other example embodiments, microlenses and chromatic filters are provided, wherein the arrangement may optionally also be used as a light diffuser or a separate light diffuser may be provided. It should also be noted that, for sake of ease of representation, like reference signs denote like components in the following example embodiments.

Figure 5:
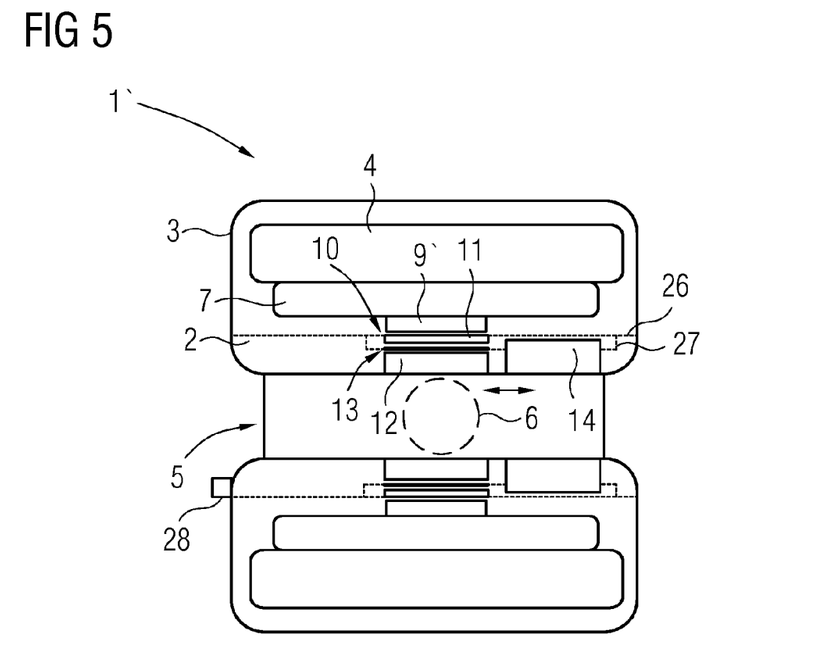
FIG. 5 shows a schematic view of a second example embodiment of an image recording device according to the invention in the first recording mode.

FIG. 5 shows a second example embodiment of an image recording device 1' according to the invention. In particular, with regard to the magnetic resonance device 2 with the magnet 4 and the gradient coil arrangement 7, this image recording device has a shell-like structure similar to the image recording device 1', but in the present case only one detector ring is provided, namely the photodetector arrangement 9'. This photodetector arrangement 9' is used in the present case both for the PET detector arrangement and for the fluorescence detector arrangement. To this end and as a further contrast to the image recording device 1, a displacement device is provided in the image recording device 1', said displacement device comprising a support 27 guided in a guide 26 and displaceable in the guide 26 by a drive device 28, which is pneumatic for example. The drive device 28 arranged outside the patient receptacle 5 in the present example may also be a hydraulic or electric drive device.

The components of the optical system 14 of the fluorescence detector arrangement are provided on the support 27 as a first displacement arrangement, and the inwardly arranged body coil 12 with the radio frequency shield 13 is provided together with the outwardly arranged optical system 10 of the PET detector arrangement, which in turn comprises an array 11 formed of scintillator blocks, as a second displacement arrangement. Both displacement arrangements are adapted to cover the entire field of homogeneity 6.

In FIG. 5 the arrangement is clearly selected so that the second displacement arrangement is located in an imaging position together with the body coil 12 and the optical system 10, so that PET image data and magnetic resonance image data can be recorded simultaneously. This may be referred to as a first mode. To be able to record MR image data and PET image data simultaneously in the first mode, the displacement device moves the optical system 14 of the fluorescence detector arrangement away from the field of homogeneity by moving the support 27 in the longitudinal direction of the patient receptacle 5, whilst the optical system 10 and the body coil 12 are arranged so as to cover the field of homogeneity 6. Since the optical system 10 is then located directly in front of the photodetectors of the photodetector arrangement 9', gamma radiation which has been converted into visible light by the scintillator blocks can be detected.

Figure 6:
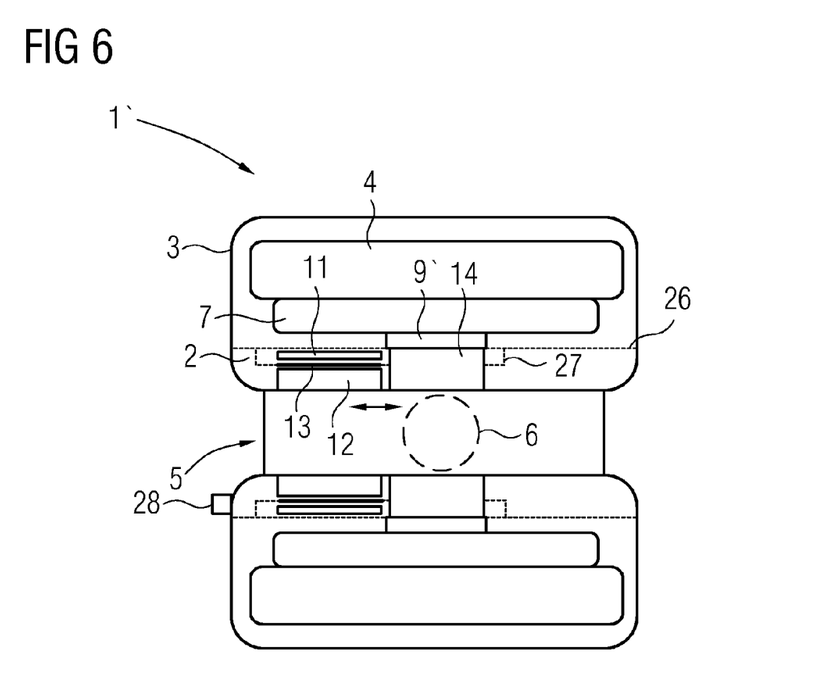
FIG. 6 shows the image recording device according to FIG. 4 in the second recording mode.

The second mode, in which only fluorescence image data is recorded, is illustrated in FIG. 6. In this case, by moving the support 27 in the guide 26, the displacement device has moved the optical system 10 and the radio frequency system 12, 13 to the left away from the field of homogeneity 6 so as to position the optical system 14 beside the photodetector arrangement 9', covering the field of homogeneity 6. Fluorescent light emitted from an object under examination can now be detected by microlenses 22, filtered and detected by the photodetectors. In this case too, the optical system 14 is also formed as a light diffuser, wherein the light sources (laser diodes or lasers) are also already contained in the optical system 14.

Figure 7:
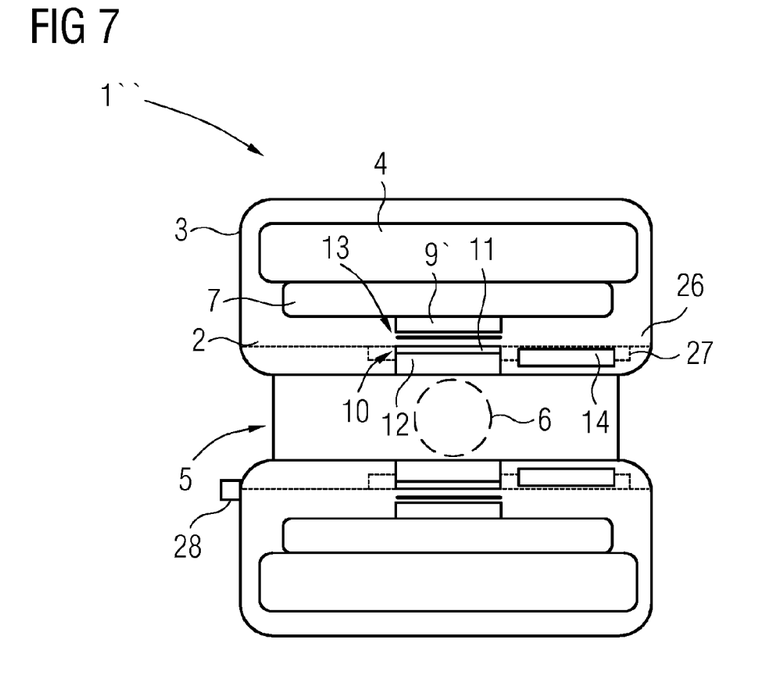
FIG. 7 shows a schematic view of a third example embodiment of an image recording device according to the invention in the first recording mode.
Figure 8:
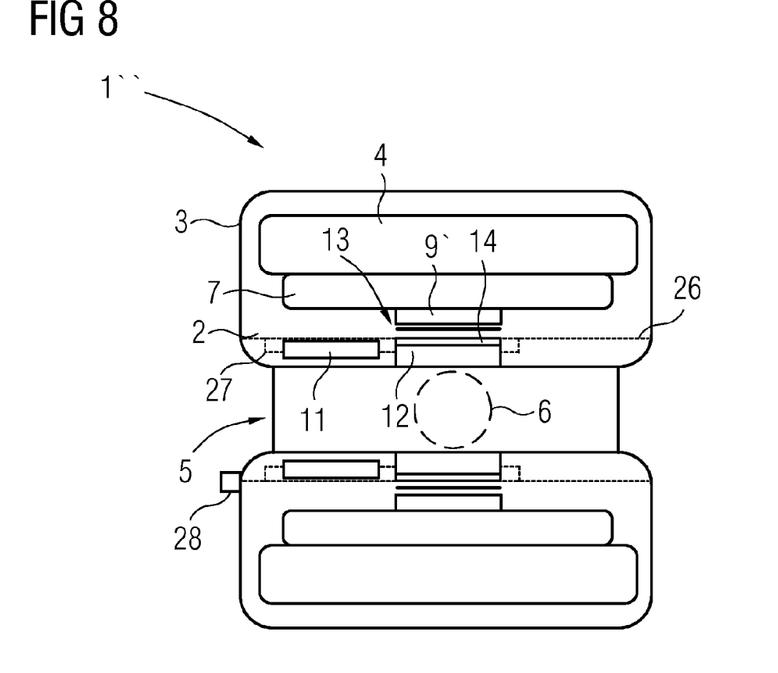
FIG. 8 shows the image recording device of FIG. 6 in the second recording mode.

FIGS. 7 and 8 show a modified embodiment of a third example embodiment of an image recording device 1", in which the body coil 12 is stationary and only the optical systems 10, 14 are displaced. A support 27 guided in a guide 26 is also used for this, wherein, in contrast to FIG. 5 and FIG. 6, magnetic resonance imaging is possible in both modes in the imaging positions shown in FIGS. 7 and 8, which means that there is a first mode in which magnetic resonance image data and PET image data can be recorded, and a second mode in which fluorescence image data and magnetic resonance image data can be recorded. To allow the latter, the radio frequency shield 13 of the body coil 12 is formed so as to be optically transparent, but electrically conductive. In this example embodiment, too, the displacement device utilizes gaps provided between the longitudinal conductors of the body coil 12 formed as a birdcage coil so that the support can shuttle between the two imaging positions, as illustrated in FIGS. 7 and 8.

Figure 9:
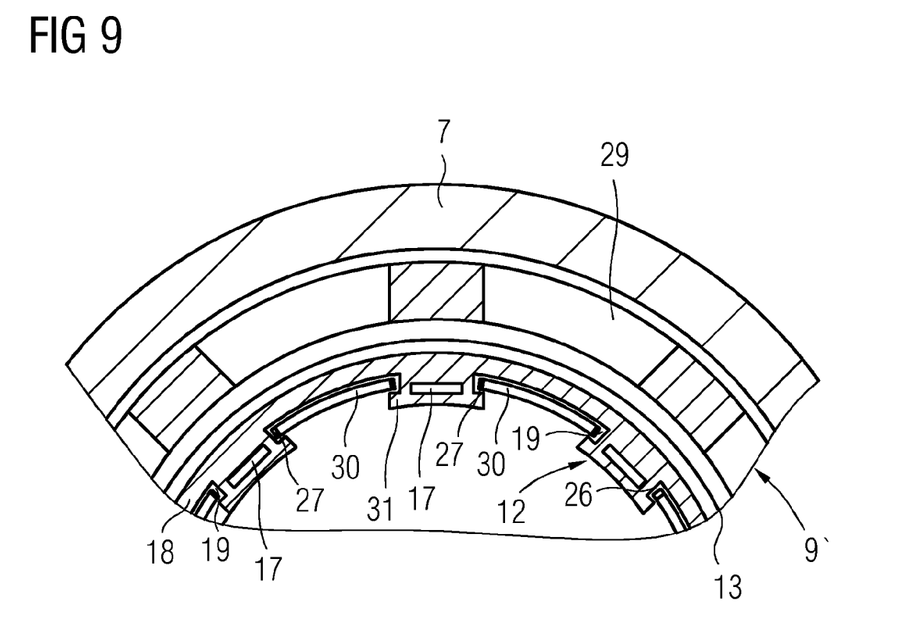
FIG. 9 shows a possible design of a displacement device.

FIG. 9 shows this in more detail in a schematic sectional view. The gradient coil arrangement 7 is not shown in greater detail radially outwardly. The gradient coil arrangement is adjoined radially inwardly by the photodetector arrangement 9', which includes the individual photodetectors 29, which are spatially resolving in the present case.

The radio frequency shield 13 of the body coil 12 lies between the support structure 18 of the body coil 12 and the photodetector arrangement 9'. Again, gaps 19 are clearly present between the longitudinal conductors 17, the components 30 of the corresponding optical system 10, 14 being mounted in said gaps and held displaceably on the support 27. In this case, the support structure 18, itself, clearly forms part of the guide 26, projections 31 holding the components 30 in place.

The photodetectors 29 are positioned in such a way that they are aligned in the radial direction behind the gaps 19. The end rings, which are not shown in greater detail in FIG. 9, are arranged in such a way that the gaps 19 can also be continued at the longitudinal edge of the body coil 12 so that the components 30 can be displaced out of the gaps 19 and into the gaps 19. The gaps 19 are continued accordingly through the guide 26 outside the body coil 12, that is to say in the longitudinal regions of the patient receptacle 5, into which the support structure 18 does not extend.

Lastly, it should be noted that in each of the example embodiments illustrated here, the optical system 14 of the fluorescence detector arrangement comprises mechanical actuators, via which the focal length or lens position can be changed to allow optimal focusing on an area of interest (the target area). The image recording devices 1, 1', 1" also comprise a control device for controlling the operation of the image recording device 1, 1', 1", the control device also being designed to control the mechanical actuators of the optical system 14. It may be that a magnetic resonance image is recorded by way of the magnetic resonance device 2 before a fluorescence image is recorded. This magnetic resonance image, which shows clearly the anatomical structure of the object under examination and therefore also the target area, is assessed with regard to the position of the target area. Following assessment of the magnetic resonance image, which may also take place automatically, the location of the target area in the coordinate system of the magnetic resonance device 2 is thus known. Depending on this information regarding the position of the target area, the mechanical actuators can then be controlled automatically so that the target area can be focused perfectly. Adaptive focusing is thus achieved.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SIGNS

1 Image recording device
1' Image recording device
1" Image recording device
2 Magnetic resonance device
3 Housing
4 Primary magnet
5 Patient receptacle
6 Field of homogeneity
7 Gradient coil arrangement
8 Photodetector arrangement
9 Photodetector arrangement
9' Photodetector arrangement
10 Optical system
11 Array
12 Body coil
13 Radio frequency shield
14 Optical system
15 Optical waveguide system
16 End rings
17 Longitudinal conductor
18 Support structure
19 Gaps
20 Microlens array
21 Plate
22 Microlenses
23 Fiber
24 Fiber bundle
25 Light diffuser
26 Guide
27 Support
28 Drive device
29 Photodetector
30 Components
31 Projections

What is claimed is:

1. An image recording device configured to simultaneously record magnetic resonance image data and nuclear medical image data, in particular PET image data, the image recording device comprising:
a nuclear medical detector arrangement integrated into a magnetic resonance device; and
a fluorescence detector arrangement, integrated into the magnetic resonance device, the fluorescence detector arrangement including an optical system and configured to perform fluorescence imaging, wherein
the image recording device has a shell-structure in which, starting from a cylindrical patient receptacle and moving radially outward, at least part of the fluorescence detector arrangement permeable to γ-photons to be detected for nuclear medical imaging is provided first followed by the nuclear medical detector arrangement.

2. The image recording device as claimed in claim 1, wherein the nuclear medical detector arrangement and the fluorescence detector arrangement are arranged, together with the magnetic resonance device, to simultaneously record data out of a target area.

3. The image recording device as claimed in claim 2, wherein the target area is a homogeneity volume of the magnetic resonance device.

4. The image recording device as claimed in claim 1, wherein the optical system of the fluorescence detector arrangement is partly made of plastic.

5. The image recording device as claimed in claim 1, wherein in the longitudinal direction of the cylindrical patient receptacle, the cylindrical patient receptacle is first adjoined in the radially outward direction by a body coil, covering a field of homogeneity of the image recording device, the nuclear medical detector arrangement following the body coil in the radially outward direction, and
the fluorescence detector arrangement includes the optical system which is integrated into the body coil, and which includes a connecting optical waveguide system designed to guide a fluorescent light received by the optical system to photodetectors of a photodetector arrangement arranged in longitudinal regions of the patient receptacle not covering the field of homogeneity or outside the magnetic resonance device.

6. The image recording device as claimed in claim 5, wherein the body coil has a radio frequency shield,
the optical system is arranged between longitudinal conductors of the body coil, and
the connecting optical waveguide system is designed to guide the fluorescent light received by the optical system to the photodetectors of the photodetector arrangement arranged in the longitudinal regions of the patient receptacle not covering the field of homogeneity, in the radial region of the nuclear medical detector arrangement.

7. The image recording device as claimed in claim 5, wherein the optical system includes a plurality of microlenses arranged in at least one microlens array.

8. The image recording device as claimed in claim 7, wherein each of the plurality of microlenses is connected to an optical fiber of the optical waveguide system.

9. The image recording device as claimed in claim 1, wherein at least one displacement device is provided for selectively bringing at least part of one of the nuclear medical detector arrangement or the fluorescence detector arrangement into an imaging position.

10. The image recording device as claimed in claim 9, wherein the imaging position covers a field of homogeneity of the magnetic resonance device.

11. The image recording device as claimed in claim 9, wherein a body coil of the magnetic resonance device is displaceable together with the nuclear medical detector arrangement.

12. The image recording device as claimed in claim 11, wherein the nuclear medical detector arrangement and the fluorescence detector arrangement are displaceable within and adjacent to a gradient coil arrangement.

13. The image recording device as claimed in claim 11, wherein the body coil includes a radio frequency shield.

14. The image recording device as claimed in claim 9, wherein another optical system, including an array of scintillator blocks, of the nuclear medical detector arrangement and the optical system of the fluorescence detector arrangement are selectively displaceable, as part of the nuclear medical detector arrangement and the fluorescence detector arrangement, in regions of a stationary body coil of the image recording device not occupied by elements of the body coil, and     a photodetector arrangement used jointly for nuclear medical imaging and fluorescence imaging adjoins the body coil in the radially outward direction.

15. The image recording device as claimed in claim 14, wherein a radio frequency shield includes an optically transparent and electrically conductive layer.

16. The image recording device as claimed in claim 14, wherein the optical system includes microlenses,     the regions of the stationary body coil not occupied by the elements of the body coil are between longitudinal conductors of the body coil, and     the photodetector arrangement adjoins a radio frequency shield of the body coil.

17. The image recording device as claimed in claim 9, wherein the at least one displacement device includes at least one guide, in which a support for displacing different components of the image recording device is guided.

18. The image recording device as claimed in claim 9, wherein the at least one displacement device includes at least one of an electric drive device, a hydraulic drive device and a pneumatic drive device, and     when the at least one displacement device is the electric drive device, electrical components of the electric drive device are arranged outside the cylindrical patient receptacle of the magnetic resonance device.

19. The image recording device as claimed in claim 1, wherein the optical system of the fluorescence detector arrangement includes at least one light diffuser for optical excitation light, said light diffuser being connected via an optical waveguide to a light source.

20. The image recording device as claimed in claim 1, wherein the optical system of the fluorescence detector arrangement includes at least one optical element which is be focused on a specific target area and which is capable of being actuated via a mechanical actuator, said mechanical actuator being controllable via a control device of the image recording device.

21. The image recording device as claimed in claim 20, wherein said mechanical actuator is controllable via the control device of the image recording device, according to an assessment of a magnetic resonance image.

\* \* \* \* \*